United States Patent [19]

Pitt

[11] 4,038,284
[45] July 26, 1977

[54] N-ACYLATION OF OXAZOLIDINES

[75] Inventor: Harold M. Pitt, Lafayette, Calif.

[73] Assignee: Stauffer Chemical Company, Westport, Conn.

[21] Appl. No.: 646,823

[22] Filed: Jan. 7, 1976

Related U.S. Application Data

[63] Continuation-in-part of Ser. No. 599,793, July 28, 1975, abandoned.

[51] Int. Cl.$^2$ ............................................. C07D 263/04
[52] U.S. Cl. .............................. 260/307 FA; 260/691
[58] Field of Search .................. 260/307 FA, 301 FA

[56] References Cited

U.S. PATENT DOCUMENTS 3,707,541  12/1972  Lajiness ........................... 260/244 R

OTHER PUBLICATIONS

Sheehan et al., J. Amer. Chem. Soc. 71 1856 (1949).
Warnhoff et al., Chem. Benchte 100, 2122 (1967).
Kent et al., Organic Syn. Collective vol. III, p. 490 (1955).
Carter et al., Organic Syn. Collective vol. III, p. 167 (1955).
Bergman, Chemical Reviews 53, 310–317, 321–324.

Primary Examiner—Donald G. Daus
Assistant Examiner—Mark L. Berch
Attorney, Agent, or Firm—Joel G. Ackerman

[57] ABSTRACT

N-substituted oxazolidines having the formula

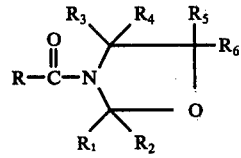

in which R is $C_1$–$C_{10}$ haloalkyl, $C_1$–$C_{10}$ alkyl or lower alkylthio; and $R_1$ and $R_2$ are independently hydrogen, $C_1$–$C_{12}$ alkyl, lower alkoxyalkyl or lower alkylol; and $R_3$, $R_4$, $R_5$ and $R_6$ are independently hydrogen, lower alkyl, lower alkoxyalkyl or lower alkylol are prepared by reacting an oxazolidine with an acid chloride or analogous compound in the presence of a hydrogen chloride acceptor and water. The process is characterized by minimization of by-product formation.

In a preferred embodiment, the oxazolidine is prepared by reaction of an alkanolamine with an aldehyde or ketone and the water of reaction is retained in the system.

14 Claims, No Drawings

N-ACYLATION OF OXAZOLIDINES

CROSS-REFERENCE TO RELATED APPLICATIONS

This application is a continuation-in-part of U.S. Ser. No. 599,793, filed July 28, 1975, now abandoned.

BACKGROUND AND PRIOR ART

This application relates to the production of oxazolidines having the formula

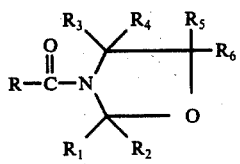

in which R is $C_1$–$C_{10}$ haloalkyl, $C_1$–$C_{10}$ alkyl or lower alkylthio; $R_1$ and $R_2$ are independently hydrogen, $C_1$–$C_{12}$ alkyl, lower alkoxyalkyl or lower alkylol; and $R_3$, $R_4$, $R_5$ and $R_6$ are independently hydrogen, lower alkyl, lower alkoxyalkyl or lower alkylol.

In describing the above group of compounds, the terms "alkyl" and "haloalkyl" include members which contain from 1 to 10 or 12, carbon atoms inclusive, as indicated, in both straight and branched chain configurations, the term "halo" including chloro or bromo with substitution being either of the mono, di, tri, tetra and/or per from. For instance, the alkyl portion may be a group such as methyl, ethyl, n-propyl, isopropyl, n-butyl, sec.-butyl,1,1,1-dimethylbutyl, amyl, isoamyl, 2,4,4-trimethylpentyl, n-hexyl, isohexyl, n-heptyl, n-octyl, isooctyl, nonyl, decyl, dimethylheptyl, and the like.

The terms "lower alkyl", "lower alkylthio", "lower alkoxyalkyl" and "lower alkylol" preferably include such groups which contain from 1 to 6, most preferably from 1 to 4 carbon atoms, inclusive, for example, methyl, ethyl, n-propyl, isopropyl, n-butyl, isobutyl, sec.-butyl, tert.-butyl, pentyl, hexyl and the like; methylthio, ethylthio, n-propylthio, isopropylthio, n-butylthio, and the like; methoxymethyl, ethyoxyethyl, hydroxymethyl, hydroxy-n-propyl, and the like.

Compounds of this type have been found to possess activity as herbicidal antidotes and, in some cases, as herbicides, and are disclosed in several publications including, for instance, Belgian Pat. Nos. 782,120, 806,038 and 806,040 and German Offenlegungsschrift No. 2,341,810. Representative examples of compounds of this type are included in Table I, hereinbelow.

TABLE I

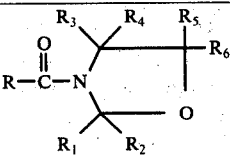

| Compound Number | R | $R_1$ | $R_2$ | $R_3$ | $R_4$ | $R_5$ | $R_6$ |
|---|---|---|---|---|---|---|---|
| 1 | $CHCl_2$ | H | H | H | H | H | H |
| 2 | $CHCl_2$ | $CH_3$ | $CH_3$ | H | H | H | H |
| 3 | $CHCl_2$ | $CH_3$ | $CH_3$ | H | H | $CH_3$ | H |
| 4 | $CHCl_2$ | $CH_3$ | $CH_3$ | H | H | $n$-$C_3H_7$ | H |
| 5 | $CH_2Cl$ | $CH_3$ | $CH_3$ | H | H | H | H |
| 6 | $CBr_3$ | $CH_3$ | $CH_3$ | H | H | H | H |
| 7 | $CH_2Br$ | $CH_3$ | $CH_3$ | $CH_3$ | $CH_3$ | H | H |
| 8 | $CHCl_2$ | $CH_3$ | $CH_3$ | $C_2H_5$ | H | H | H |
| 9 | $CCl_3$ | $CH_3$ | H | H | H | $CH_3$ | H |
| 10 | $CCl_3$ | $C_2H_5$ | H | $C_2H_5$ | H | H | H |
| 11 | $CHCl_2$ | $CH_3$ | $CH_3$ | $CH_3$ | $CH_3$ | H | H |
| 12 | $CHCl_2$ | $CH_3$ | $t$-$C_4H_9$ | H | H | H | H |
| 13 | $CHCl_2$ | H | H | $CH_3$ | $CH_3$ | H | H |
| 14 | $CBr_3$ | H | H | $C_2H_5$ | H | H | H |
| 15 | $CHCl_2$ | $CH_3$ | $i$-$C_3H_7$ | H | H | H | H |
| 16 | $CBr_3$ | $CH_3$ | $C_2H_5$ | H | H | H | H |
| 17 | $CBr_3$ | $C_2H_5$ | H | H | H | H | H |
| 18 | $CH_3CHBr$ | $CH_3$ | $CH_3$ | H | H | $CH_3$ | H |
| 19 | $CH_3CHBr$ | $C_2H_5$ | H | H | H | $CH_3$ | H |
| 20 | $CH_2Br$ | $CH_3$ | $CH_3$ | $C_2H_5$ | H | H | H |
| 21 | $CH_2Br$ | $CH_3$ | H | H | H | H | H |
| 22 | $CH_3(CHBr)_4$ | $CH_3$ | $CH_3$ | H | H | H | H |
| 23 | $ClCH_2CH_2$ | $CH_3$ | $CH_3$ | H | H | H | H |
| 24 | $CH_2BrCHBr$ | $CH_3$ | $t$-$C_4H_9$ | H | H | H | H |
| 25 | $CHBr_2$ | $C_2H_5$ | H | H | H | H | H |
| 26 | $(CH_3)_2CBr$ | $C_2H_5$ | H | H | H | $CH_3$ | H |
| 27 | $CCl_3$ | $CH_3$ | H | H | H | H | H |
| 28 | $CH_2BrC(CH_3)Br$ | $CH_3$ | H | H | H | $CH_3$ | H |
| 29 | $CH_2BrCH_2$ | $CH_3$ | $CH_3$ | H | H | H | H |
| 30 | $Cl(CH_2)_3$ | $CH_3$ | $CH_3$ | H | H | H | H |
| 31 | $CH_3CHClCH_2$ | $CH_3$ | $CH_3$ | H | H | H | H |
| 32 | $C_2H_5CHBr$ | $CH_3$ | $CH_3$ | H | H | $CH_3$ | H |
| 33 | $C_3H_7CHBr$ | $CH_3$ | $CH_3$ | H | H | H | H |
| 34 | $CH_2ClCH_2CH_2$ | $CH_3$ | $CH_3$ | H | H | $CH_3$ | H |
| 35 | $CH_2Br(CH_2)_4$ | $CH_3$ | $CH_3$ | H | H | $CH_3$ | H |
| 36 | $C_2H_5S$ | H | H | $C_2H_5$ | H | H | H |
| 37 | $C_2H_5S$ | $CH_3$ | H | H | H | $CH_3$ | H |
| 38 | $C_3H_7S$ | $CH_3$ | $CH_3$ | $C_2H_5$ | H | H | H |
| 39 | $i$-$C_3H_7S$ | $CH_3$ | $CH_3$ | $C_2H_5$ | H | H | H |
| 40 | $CH_3S$ | $CH_3$ | H | $C_2H_5$ | H | H | H |
| 41 | $n$-$C_4H_9S$ | $CH_3$ | $CH_3$ | $C_2H_5$ | H | H | H |
| 42 | $C_6H_{13}$ | $CH_3$ | $CH_3$ | H | H | H | H |
| 43 | $CHCl_2$ | $C_3H_7$ | H | H | H | H | H |
| 44 | $CHCl_2$ | $CH_3OCH_2$ | H | H | H | H | H |
| 45 | $CH_2Cl$ | $CH_3$ | $CH_3$ | H | H | $n$-$C_3H_7$ | H |

TABLE I-continued

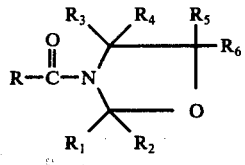

| Compound Number | R | $R_1$ | $R_2$ | $R_3$ | $R_4$ | $R_5$ | $R_6$ |
|---|---|---|---|---|---|---|---|
| 46 | $CHCl_2$ | $CH_3$ | $CH_3$ | $CH_3$ | $CH_2OH$ | H | H |
| 47 | $CH_2Cl$ | $n$-$C_5H_{11}$ | H | $CH_3$ | $CH_3$ | H | H |
| 48 | $CH_2Cl$ | 2.6-dimethylheptyl | H | $CH_3$ | $CH_3$ | H | H |
| 49 | $CH_2Cl$ | $n$-$C_3H_7$ | $CH_3$ | $CH_3$ | $CH_3$ | H | H |
| 50 | $CH_2Cl$ | $C_2H_5$ | $C_2H_5$ | $CH_3$ | $CH_3$ | H | H |
| 51 | $CH_2Cl$ | $n$-$C_3H_7$ | $n$-$C_3H_7$ | $CH_3$ | $CH_3$ | H | H |

In one preferred embodiment, $R_1$ and $R_2$ are independently hydrogen, lower alkyl, lower alkoxyalkyl or lower alkylol.

Additional compounds of this type are disclosed in the copending U.S. Pat. application No. 566,019 of Eugene G. Teach, filed Apr. 7, 1975, now U.S. Pat. No. 3,959,304.

According to the prior art, oxazolidines were generally prepared by the condensation of alkanolamines with a suitable aldehyde or ketone in a solvent such as benzene, with water being removed from the reaction product. Such a method is described, for instance, in the article by Bergmann et al., JACS 75 358 (1953). In order to product N-substituted oxazolidines of the formula shown above, the product of this reaction was further treated with an acid chloride in the presence of a hydrogen chloride acceptor, such as triethylamine. This reaction was conducted in the anhydrous state, the water having been removed after the condensation of the alkanolamine with the carbonyl compound. Processes of this type, for example, are described in the above-mentioned Belgian patents.

Substituted oxazolidines produced in this manner are frequently contaminated with by-products, generally resulting from the reaction of the acid chloride with by-products or reaction intermediates formed during the condensation step. These by-products have often proved difficult to separate either because of their quantity or their chemical behavior, or both. In the production of substituted oxazolidines on a small scale, such as for laboratory or testing purposes, the desired product can be obtained in the substantially pure state with sufficient purification. Such purification steps, however, may result in sufficient product loss as to be detrimental if the desired product is to be produced on a larger scale, for instance, commercially. Furthermore, the elimination or reduction of such purification steps would be advantageous in a commercial facility since the installed and/or operating cost could be reduced by the cost of equipment and/or solvent not required.

It is an object of the present invention to provide an improved process for the production of oxazolidines.

A further object of the present invention is to provide an improved process for the production of N-substituted oxazolidines.

Another object of the present invention is to provide a process for the production of N-substituted oxazolidines of adequate purity.

Yet a further object of the present invention is to provide a process for the production of N-substituted oxazolidines requiring fewer purification steps than previously.

Still another object of the present invention is to provide a process for the production of N-substituted oxazolidins in which the production of undesirable by-products can be minimized.

SUMMARY OF THE INVENTION

The present invention comprises a process for the production of N-substituted oxazolidines having the formula

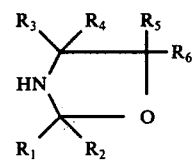

wherein R is $C_1$-$C_{10}$ haloalkyl, $C_1$-$C_{10}$ alkyl or lower alkylthio; $R_1$ and $R_2$ are independently hydrogen, $C_1$-$C_{12}$ alkyl, lower alkoxyalkyl or lower alkylol and $R_3$, $R_4$, $R_5$ and $R_6$ are independently hydrogen, lower alkyl, lower alkoxyalkyl or lower alkylol, comprising reacting an oxazolidine having the formula

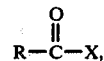

with a compound having the formula $$R-\overset{O}{\underset{\|}{C}}-X,$$

in which X is a halogen, in the presence of a hydrogen chloride acceptor and water.

In a preferred embodiment, the invention herein comprises a process for production of N-substituted oxazolidines having the above formula comprising the steps of:

a. Reacting an alkanolamine having the formula

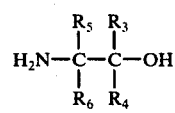

with a carbonyl compound having the formula

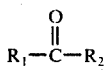

to produce water and a reaction product comprising an oxazolidine, formula

b. reacting the oxazolidine in the presence of water and a hydrogen chloride acceptor, with a compound having the formula
in which X is a halogen, and c. recovering the N-substituted oxazolidine from the product of (b).

DETAILED DESCRIPTION OF THE INVENTION

As is known in the prior art, when an alkanolamine is condensed with an aldehyde or ketone, the resulting product is an oxazolidine. However, the oxazolidine is believed to be in equilibrium with an isomer in the form of a Schiff base. For example, the reaction of ethanolamine with acetone in the presence of a solvent such as benzene produces a mixture of 2,2-dimethyloxazolidine and an isomeric Schiff base having the formula

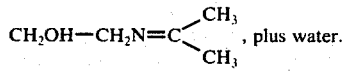

Longer chain alkanolamines, in which the hydroxyl group is attached to the carbon atom adjacent to the amino group, react in a similar fashion, resulting in oxazolidines containing various substituents on the ring. Generally both the desired oxazolidine and the undesired isomeric Schiff base are present in the reaction mixture. In the prior art, water is removed from the reaction mixture by stripping or distillation and the remaining products reacted in an anhydrous system with an acid chloride of the formula

to produce an N-substituted oxazolidine, plus hydrogen chloride.

However, the Schiff base will also react with the acid chloride, producing undesirable by-products of various types, believed to be primarily esters. These must be separated from the desired N-substituted oxazolidine in order for the latter to be used either commercially or otherwise. In a number of cases, a good separation is difficult to achieve; in others, it can be achieved, but may require several purification steps.

It has now been found, however, if, contrary to the prior art practice, the reaction of the oxazolidine and acid chloride is conducted in the presence of water, the purity of the substituted oxazolidine obtained is substantially greater, permitting purification with fewer steps. Additionally, the yield of the desired oxazolidine may also be increased.

Without intending to bind myself to a theory, it is believed that the condensation of the carbonyl compound and alkanolamine proceeds through an intermediate diol compound which may lose water in two ways, forming either the oxazolidine or the Schiff base. It is believed that in the presence of water, such as the water of reaction, the equilibrium between the intermediate and the two potential products is balanced in favor of the oxazolidine. Alternatively, it may be that, in aqueous solution, the Schiff base is far less reactive than the oxazolidine, and that addition of the acid chloride will react preferentially with the oxazolidine, which in turn causes decomposition of the Schiff base and formation of additional oxazolidine.

In one preferred embodiment, the water produced during condensation of the alkanolamine with the aldehyde or ketone is retained in the reaction system and the total reaction products (including the oxazolidine and water) are contacted with an acid chloride in the presence of a hydrogen chloride acceptor.

In another embodiment, water is removed from the condensation reaction products, but is re-introduced into the system in the form of an aqueous solution of a hydrogen chloride acceptor such as sodium hydroxide.

In another preferred embodiment, an aqueous solution of caustic containing about 5 – 50% NaOH is added to the system prior to addition of the acid chloride. The strong base serves to function as the hydrogen chloride acceptor in the following step and is also believed to be effective in lowering the water vapor pressure over the reaction system, promoting the formation of the oxazolidine from the diol intermediate, rather than the Schiff base. A 20% NaOH solution is preferred, since at a higher concentration sodium chloride is precipitated from the system, which may require diluting the mixture before purification.

Another advantage of the present process is that since the reaction of the oxazolidine and the acid chloride are conducted in aqueous solution, it is not necessary to utilize comparatively expensive hydrogen chloride acceptors such as triethylamine, although these can be used as they will serve to effectuate this reaction. The hydrogen chloride acceptor utilized may be a less expensive substance, for example, a weak caustic solution, or another alkali metal hydroxide such as potassium hydroxide (in aqueous solution). Most common hydrogen chloride acceptors are miscible with or soluble in water under the conditions employed; however, water-immiscible hydrogen chloride acceptors such as dimethylaniline may be used. As mentioned above, if an aqueous caustic solution is added to the reaction product prior to the addition of the acid chloride, this caustic will also serve to function as the hydrogen chloride acceptor.

In another preferred embodiment, the reaction is run at low temperatures, such as −5 to +5° C. However, the reaction an be run at somewhat higher temperatures, for example, up to about 25° C, though at these temperatures the product yield may be somewhat less. The alkanolamine use can be any lower alkanolamine, that is one having from about 2 to about 6 carbon atoms, provided that the hydroxyl group and amino group are attached to adjacent carbon atoms. The carbonyl compound can be any suitable aldehyde or ketone of the formula $R_1COR_2$ in which $R_1$ and $R_2$ are independently hydrogen, $C_1$-$C_{12}$ alkyl, lower alkoxyalkyl or lower alkylol, preferably having from 1 to 4 carbon atoms. The following examples are presented as illustrative of the invention without intending to limit the scope thereof.

Preparation of 2,2-dimethyl-3-dichloroacetyl oxazolidine (Compound 2 in the Table)

EXAMPLE 1 (Prior Art)

Five and one-tenth (5.1) grams of 2,2-dimethyl oxazolidine dissolved in 50 ml. of benzene was treated with 5.5 g. of triethylamine and 7.4 g. of dichloroacetyl chloride was added dropwise with stirring and cooling in an ice bath. The mixture was poured into water, the benzene solution separated, dried over anhydrous magnesium sulfate and the solvent stripped under vacuum. The product was a waxy solid which had a melting point of 113°–115° C on recrystallization from diethyl ether.

EXAMPLE 2

122 ml. (122 g) ethanolamine, 150 ml. acetone and 600 ml. benzene were introduced into a 2-leter reactor. The mixture was heated to reflux, water was stripped off, the reaction mixture was allowed to cool, and 200 ml. of 37% NaOH and 175 ml. of water were added. The mixture was maintained at about 5° C while 100 ml. of dichloroacetyl chloride was added. The mixture was let stand for 1 hour, then an additional 93 ml. of dichloroacetyl chloride was added. The pH of the mixture dropped to below 13 and 25 ml. of 20% NaOH was added, bringing the pH up to 13.8. The reaction product was neutralized with concentrated hydrochloric acid; benzene was stripped off and the product filtered and dried. There was obtained 282 g (66.7% of theoretical) of a solid, m.p. 117.5°–119.5° C.

EXAMPLE 3

122 ml. (122 g) ethanolamine, 150 ml. (116 g) acetone and 600 ml. benzene were introduced into a 2-liter reactor. The reaction proceeded at a temperature of about 33°–34° C. The reaction mixture was stirred for 1 hour, 200 ml. of 33% NaOH were added, the temperature lowered to about 5° C with an acetone-ice bath and the mixture stirred for 3 more hours. 110 ml. (168.5 g) of dichloroacetyl chloride was added over a period of 1 hour followed by 25 ml. of 33% NaOH and a second portion of 110 ml. of dichloroacetyl chloride (slowly added). The reaction product was neutralized with concentrated hydrochloric acid. Water (190 ml.) was added to dissolve the sodium chloride formed, benzene was stripped off and the product filtered and dried. There was obtained 347 g (82% of theoretical) m.p. 117.5°–119° C.

Preparation of 2,2,5-trimethyl-3-dichloroacetyl oxazolidine (Compound 3 in Table)

EXAMPLE 4 (Prior Art)

Eighteen (18) milliliters of a benzene solution containing 4.6 g. of 2,2,5-trimethyl oxazolidine was added to 25 ml. of benzene and 4.5 g. of triethylamine. Five and nine-tenths (5.9 ) grams of dichloroacetyl chloride was added dropwise with stirring and cooling in an ice bath. When reaction was complete the mixture was poured into water and the benzene layer separated, dried over anhydrous magnesium sulfate and the benzene removed under vacuum. Yield was 7.7 g. of an oil, $n_D^{30} = 1.4950$.

EXAMPLE 5

150 g. (162 ml.) of isopropanolamine, density 0.961, was mixed with 150 ml. (116 g) acetone and 600 ml. benzene. Water was stripped off, the reaction mixture cooled down and 200 ml. of 20% of NaOH and 175 ml. of water were mixed with the products. Subsequently, 202 ml. (310 g) of 96% pure dichloroacetyl chloride was added. Temperature was maintained at 5° C. The reaction product was neutralized with concentrated hydrochloric acid, transferred to a separatory funnel and washed once with distilled water. Benzene was stripped off. 343 g. of 2,2,5-trimethyl-3-dichloroacetyl oxazolidine were recovered (76% of theoretical), melting point 77°–84° C.

EXAMPLE 6

150 g. (162 ml.) of isopropanolamine, 150 ml. (116 g) of acetone and 600 ml. of benzene were introduced into a 2-liter reactor. The products were heated to 40° and stirred for an hour. 200 ml. of 33% sodium hydroxide was added and the resulting mixture stirred for two more hours. The resulting mixture was chilled at 5° C with an ice bath using acetone and 110 ml. of dichloroacetyl chloride was slowly added over a period of 1 hour. The mixture was allowed to stand for one and a half hours more and then 110 additional ml. of dichloroacetyl chloride were added over another hour's time, together with an additional 10 ml. of 33% NaOH. The pH of the reaction product was 11.1. The reaction products were neutralized with hydrochloric acid until the pH was about 3. Water (185 ml.) was added to dissolve the sodium chloride formed. Benzene was stripped off under vacuum. The product was filtered, stripped and dried without further crystallization. 346.2 g. were recovered (77% of theoretical), melting point 87°–88° C.

As can be seen from the examples, the use of either embodiment of the present invention produced a product of greater purity than the use of the prior art technique of operating in an anhydrous system. In the preparation of 2,2-dimethyl-3-dichloroacetyl oxazolidine (Compound 2), removal of water from the system, followed by its re-introduction in the form of an aqueous caustic solution (as in Example 2) produced a much purer product than by the prior art technique of Example 1 and the product did not require recrystallization. When the water was retained in the system (Example 3) the same purer product was obtained, in higher yield.

Similar results as seen by comparing the production of 2,2,5-trimethyl-3-dichloroacetyl oxazolidine (Compound 3) in Examples 4–6. Both methods according to the invention resulted in a crystalline product, whereas the earlier technique produced an oil, a much more impure product. Retaining the water in the system (Example 6) produced the product of highest purity.

What is claimed is:

1. A process for the production of N-substituted oxazolidines having the formula

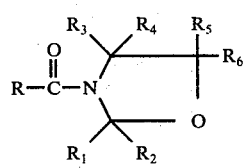

in which R is $C_1$–$C_{10}$ haloalkyl, $C_1$–$C_{10}$ alkyl or lower alkylthio, $R_1$ and $R_2$ are independently hydrogen, $C_1$–$C_{12}$ alkyl, lower alkoxyalkyl or lower alkylol, and $R_3$, $R_4$, $R_5$ and $R_6$ are independently hydrogen, lower alkyl, lower alkoxyalkyl or lower alkylol, comprising the step or reacting an oxazolidine having the formula $$\begin{array}{c} R_3 \quad R_4 \quad R_5 \\ \phantom{HN}\diagdown\phantom{|}\diagup\phantom{|}\diagdown \phantom{R_6} \\ HN\phantom{xxxxxx}R_6 \\ \phantom{HN}\diagup\phantom{xx}\diagdown\phantom{x}| \\ \phantom{xxxxxxxxx}O \\ R_1 \quad R_2 \end{array}$$

with a compound having the formula $$R-\overset{\overset{O}{\|}}{C}-X,$$

in which X is a halogen, in the presence of an alkali metal hydroxide and water.

2. A process according to claim 1 in which the temperature is between about −5° and about +5° C.

3. A process according to claim 1 in which the N-substituted oxazolidine is 2,2-dimethyl-3-dichloroacetyl, 5-n-propyl oxazolidine.

4. A process according to claim 3 in which the alkali metal hydroxide is sodium hydroxide.

5. A process according to claim 1 in which the N-substituted oxazolidine is 2,2-dimethyl-3-dichloroacetyl oxazolidine.

6. A process according to claim 1 in which the N-substituted oxazolidine is 2,2,5-trimethyl-3-dichloroacetyl oxazolidine.

7. A process for the production of N-substituted oxazolidines having the formula $$R-\overset{\overset{O}{\|}}{C}-N \begin{array}{c} R_3 \quad R_4 \quad R_5 \\ \diagdown\phantom{|}\diagup\phantom{|}\diagdown R_6 \\ \phantom{xxxxxxx}| \\ \phantom{xxxxxxx}O \\ R_1 \quad R_2 \end{array}$$

in which R is $C_1$-$C_{10}$ haloalkyl, $C_1$-$C_{10}$ alkyl or lower alkylthio, $R_1$ and $R_2$ are independently hydrogen, $C_1$-$C_{12}$ alkyl, lower alkoxyalkyl or lower alkylol, and $R_3$, $R_4$, $R_5$ and $R_6$ are independently hydrogen, lower alkyl, lower alkoxyalkyl or lower alkylol comprising the steps of:

a. reacting an alkanolamine having the formula $$H_2N-\overset{\overset{R_5}{|}}{\underset{\underset{R_6}{|}}{C}}-\overset{\overset{R_3}{|}}{\underset{\underset{R_4}{|}}{C}}-OH$$

with a carbonyl compound having the formula $$R_1-\overset{\overset{O}{\|}}{C}-R_2$$

to produce water and a reaction product comprising an oxazolidine;

b. retaining the water in contact with the reaction product of (a); and, c. reacting the reaction product of (a), in the presence of the water and an alkali metal hydroxide, with a compound having the formula $$R-\overset{\overset{O}{\|}}{C}-X,$$

in which X is halogen.

8. A process according to claim 7 further comprising (d) recovering the N-substituted oxazolidine from the product of step (c).

9. A process according to claim 8 in which step (c) is conducted at a temperature of between about −5 and about +5° C.

10. A process according to claim 7 in which the N-substituted oxazolidine is 2,2-dimethyl,3-dichloroacetyl, 5-n-propyl oxazolidine.

11. A process according to clam 7 in which the alkali metal hydroxide is sodium hydroxide.

12. A process according to claim 7 in which an aqueous solution of an alkali metal hydroxide is added to the system prior to conducting step (c).

13. A process according to claim 7 in which the N-substituted oxazolidine is 2,2-dimethyl, 3-dichloroacetyl oxazolidine.

14. A process according to claim 7 in which the N-substituted oxazolidine is 2,2,5-trimethyl1,3-dichloroacetyl oxazolidine.

* * * * *

UNITED STATES PATENT AND TRADEMARK OFFICE
CERTIFICATE OF CORRECTION

PATENT NO. : 4,038,284
DATED : July 26, 1977
INVENTOR(S) : Harold M. Pitt

It is certified that error appears in the above-identified patent and that said Letters Patent are hereby corrected as shown below:

Column 2, line 3, change "or" to ---and---.
Column 3, line 30, change "product" to ---produce---.
Column 4, line 21, change "azolidins" to ---azolidines---.
Column 5, line 7, delete the word "formula".
Column 5, lines 8 to 10, the formula contained in this space should appear after the words "having the formula" presently at Column 5, line 14.
Column 6, line 55, please change "and" to ---can---.

Claim 1, column 8, line 68, change "or" to ---of---.
Claim 4, column 9, line 22, change "3" to ---1---.
Claim 7, column 10, line 25, after the words "X is" insert ---a---.

UNITED STATES PATENT AND TRADEMARK OFFICE
CERTIFICATE OF CORRECTION

PATENT NO. : 4,038,284
DATED : July 26, 1977
INVENTOR(S) : Harold M. Pitt

It is certified that error appears in the above-identified patent and that said Letters Patent are hereby corrected as shown below:

Claim 9, column 10, line 29, change "8" to ---7---.
Claim 14, column 10, line 44, change "trimethyll" to ---trimethyl---.

Signed and Sealed this

Seventh Day of February 1978

[SEAL]

Attest:

RUTH C. MASON
Attesting Officer

LUTRELLE F. PARKER
Acting Commissioner of Patents and Trademarks